US012788601B2

(12) United States Patent
D'Hiver et al.

(10) Patent No.: US 12,788,601 B2
(45) Date of Patent: Nov. 10, 2026

(54) ORTHOSIS COMPRISING A MECHANICAL HIP LINK WITH THREE DEGREES OF FREEDOM

(71) Applicant: WANDERCRAFT, Paris (FR)

(72) Inventors: Yoann D'Hiver, Montrouge (FR); Maxime Beck, Clichy (FR); Malo Donat, Paris (FR)

(73) Assignee: WANDERCRAFT, Paris (FR)

( * ) Notice: Subject to any disclaimer, the term of this patent is extended or adjusted under 35 U.S.C. 154(b) by 244 days.

(21) Appl. No.: 18/860,117

(22) PCT Filed: Apr. 25, 2023

(86) PCT No.: PCT/EP2023/060765
§ 371 (c)(1),
(2) Date: Oct. 25, 2024

(87) PCT Pub. No.: WO2023/208904
PCT Pub. Date: Nov. 2, 2023

(65) Prior Publication Data

US 2025/0186232 A1 Jun. 12, 2025

(30) Foreign Application Priority Data

Apr. 27, 2022 (FR) ........................................ 2203952

(51) Int. Cl.
*A61F 5/01* (2006.01)
*A61H 3/00* (2006.01)

(52) U.S. Cl.
CPC ............ *A61F 5/0102* (2013.01); *A61H 3/00* (2013.01); *A61F 2005/0137* (2013.01); *A61H 2003/007* (2013.01)

(58) Field of Classification Search
CPC ............ A61F 5/0102; A61F 2005/0137; A61F 2005/0141; A61H 3/00; A61H 2003/007;
(Continued)

(56) References Cited

U.S. PATENT DOCUMENTS

2014/0358053 A1* 12/2014 Triolo .................... B25J 9/0006
602/19
2017/0143573 A1* 5/2017 Boulanger ............. A61H 1/024
(Continued)

FOREIGN PATENT DOCUMENTS

FR 3086709 A1 4/2020

OTHER PUBLICATIONS

French Search Report in related French Application No. FR 2203952, mailed Dec. 9, 2022.

(Continued)

*Primary Examiner* — Nitin Patel
(74) *Attorney, Agent, or Firm* — Thomas Horstemeyer LLP

(57) ABSTRACT

The present invention relates to an orthosis (1) comprising a mechanical hip connection (4) comprising a frontal pivot link (10), a sagittal pivot link (20) and a transverse pivot link (30) made up of a plurality of pivot links (31-37) connected in pairs by connecting rods (38-45) so as to form a virtual pivot link (30) such that the transverse pivot axis (X3) intersects the volume delimited by the sagittal plane (P1), by a plane (P4) normal to the frontal pivot axis (X2) and comprising the sagittal pivot axis (X1), by the hip structure (2) and by the leg structure (3).

20 Claims, 9 Drawing Sheets

(58) Field of Classification Search
CPC ............ A61H 1/0244; A61H 2201/165; A61H 2201/1676
See application file for complete search history.

(56) References Cited

U.S. PATENT DOCUMENTS

| | | | | |
|---|---|---|---|---|
| 2018/0125692 | A1* | 5/2018 | Takenaka | A61F 5/0102 |
| 2019/0254908 | A1* | 8/2019 | Ortlieb | A61H 1/0237 |
| 2020/0069989 | A1* | 3/2020 | Lilley | A63B 21/00178 |
| 2020/0406449 | A1* | 12/2020 | Bilodeau | B25J 9/104 |

OTHER PUBLICATIONS

PCT Search Report in related PCT Application No. PCT/EP2023/060765, mailed Jun. 2, 2023.

* cited by examiner

ORTHOSIS COMPRISING A MECHANICAL HIP LINK WITH THREE DEGREES OF FREEDOM

CROSS REFERENCE TO RELATED APPLICATIONS

This application is the 35 U.S.C. § 371 national stage application of PCT Application No. PCT/EP2023/060765, filed Apr. 25, 2023, which application claims the benefit of French Application No. FR 2203952 filed Apr. 27, 2022, both of which are hereby incorporated by reference herein in their entireties.

TECHNICAL FIELD

The present disclosure relates to a system for assisting with the mobility of a person, or exoskeleton, capable in particular of supporting a user affected by a motor deficiency.

BACKGROUND

An exoskeleton generally comprises a pelvis structure, two leg structures, two foot structures and two hip structures. The pelvis structure is configured to be positioned behind the kidneys of a user when he is wearing the exoskeleton and can be attached to the pelvis by means of a harness or straps to the body of the user. Each leg structure is configured to be positioned facing one of the legs (left or right, depending on the structure) of the user, and comprises an upper leg segment and a lower leg segment, arranged to face the thigh and the calf of the user, respectively. Each foot structure comprises, moreover, a support plane on which one of the feet (left or right, depending on the structure) of the user can be supported when the foot is laid flat. Finally, each hip structure is configured to be positioned facing one of the hips (left or right, depending on the structure).

The complete control of the exoskeleton necessitates mechanical actuators and connections to allow the movement of the exoskeleton and thus allow movement of the user wearing the exoskeleton. The mechanical connections generally comprise pivot, slide and/or ball joint links, while the actuators can comprise in particular rams or motors.

These mechanical links and actuators are selected so as to allow the movement of the exoskeleton without risking injuring the user who wears it. To this end, it is important in particular not to apply forces that are not tolerated by the members of the user and to propose an exoskeleton having both small bulk and moderate weight.

In order to allow walking movement, the exoskeleton comprises in particular mechanical hip links configured to connect the hip structure and each leg structure. Generally, these mechanical links comprise a pivot link configured to allow bending/extension movements in the sagittal plane of the user. Certain exoskeletons can comprise an additional pivot link configured to allow abduction/adduction movements in the frontal plane. The pivot axes of these mechanical links are near the pivot axes of the hip of the user and the pivot links are mounted on the exoskeleton so as to extend to the periphery of the body of the user. The user can thus move forward or rearward in the exoskeleton.

Some exoskeletons, like the Atalante exoskeleton marketed by the Applicant, also comprise a third pivot link configured to allow internal/external rotation movement in the transverse plane of the user. However, to reproduce the transverse pivot link of a human being, this pivot link should be positioned within the exoskeleton, in the location where the patient is found. The third pivot link of the Atalante exoskeleton has therefore been offset onto the rear portion of the exoskeleton. However, this offset has the consequence of generating parasitic movements of the user (his pelvis must advance during external rotation movement) and also involves limiting the articulation of the leg structure relative to the hip structure to twenty or so degrees in the transverse plane to avoid any risk of injury to the user resulting from these parasitic movements. The possible movements of the exoskeleton, and therefore of the user, though improved in comparison with mechanical links deprived of a transverse link, can still be optimized.

SUMMARY

One object of the present application is to correct the aforementioned disadvantages, by proposing an orthosis for a living being, preferably a human being, comprising a mechanical hip link capable of allow additional movements the frontal, sagittal and transverse plane, which is more ergonomic and more anthropomorphic than known orthoses.

It is proposed, according to a first aspect, an orthosis comprising a mechanical hip link connecting a hip structure configured to be positioned facing a hip of a user and a leg structure configured to receive a leg of the user, the mechanical hip link comprising a frontal pivot link configured to allow rotation movement of the leg structure relative to the hip structure along a frontal pivot axis of the orthosis, a sagittal pivot link configured to allow rotation movement of the leg structure relative to the hip structure along a sagittal pivot axis of the orthosis and a transverse pivot link configured to allow rotation movement of the leg structure relative to the hip structure along a transverse pivot axis of the orthosis. In addition, the sagittal pivot axis and the frontal pivot axis being concurrent. Moreover, the transverse pivot link being composed of a plurality of pivot links connected two by two by connecting rods so as to form a virtual pivot link so that the transverse pivot axis intersects the volume delimited by the sagittal plane, by a plane normal to the frontal pivot axis and comprising the sagittal pivot axis, by the hip structure and by the leg structure.

Preferred but non-limiting features of the orthosis according to the first aspect are the following, taken individual or in combination:

- the transverse pivot axis is normal to a plane formed by the frontal pivot axis and the sagittal pivot axis, a first intersection point defined by the intersection between the plane and the transverse pivot axis being located at a distance less than 150 mm from a second intersection point defined by the intersection of the sagittal and frontal pivot axes, preferably less than 120 mm, preferably less than or equal to 100 mm, for example less than or equal to 92 mm;
- the first intersection point is located at a distance less than or equal to 90 mm from the sagittal plane of the orthosis, preferably less than or equal to 60 mm, more preferably less than or equal to 40 mm, for example greater than or equal to 0 mm and less than or equal to 10 mm;
- the first intersection point is located at a distance less than or equal to 90 mm from a plane parallel to the frontal plane of the orthosis and comprising the sagittal pivot axis, preferably less than or equal to 70 mm;
- the pivot links composing the transverse pivot link comprise:
  - two first pivot links connected by a first connecting rod;

- a second and a third pivot link each connected to a first corresponding pivot link by a second and a third connecting rod, respectively, the second and the third connecting rods having the same length;
- a fourth pivot link connected to the second pivot link by a fourth connecting rod which is fixedly joined to the second connecting rod;
- a fifth and sixth pivot link connected respectively to the second pivot link and to the fourth pivot link by a fifth and a sixth connecting rod, respectively, the fifth and the sixth connecting rods having the same length;
- a seventh connecting rod connecting the second and the third pivot link and being fixedly joined to the fifth connection rod; and
- an eighth connecting rod connecting the fifth and the sixth pivot link;

the frontal pivot link is mechanically connected to the hip structure, the sagittal pivot link is mechanically connected to the leg structure, and the transverse pivot link is mechanically connected to the frontal pivot link and to the sagittal pivot link;

the orthosis also comprises a transverse actuator configured to actuate the transverse pivot link, a frontal actuator configured to actuate the frontal pivot link and a sagittal actuator configured to actuate the sagittal pivot link, the transverse actuator, the frontal actuator and the sagittal actuator being independent of one another;

the orthosis also comprises a transverse actuator configured to actuate the transverse pivot link, the transverse actuator comprising an actuating connecting rod including a first end connected to the transverse pivot link by means of a first ball joint link and a second end connected to the hip structure by means of a second ball joint link;

the second ball joint link is offset relative to the frontal pivot axis;

the transverse actuator comprises an actuating turntable coaxial with the frontal pivot axis;

the second ball joint link is connected to the actuator turntable while being offset relative the frontal pivot axis;

the sagittal pivot axis of the sagittal pivot link moves with a center of rotation of the first ball joint link;

the orthosis also comprises a frontal actuator configured to actuate the frontal pivot link, the frontal actuator being offset relative to the frontal pivot axis;

the frontal actuator comprises two cables mounted crossing on an output shaft of the frontal actuator, on the one hand, and on the other hand on the frontal pivot link in order to pivot the frontal pivot link around the frontal pivot axis;

the orthosis also comprises at least one of the following mechanical stops: a frontal stop configured to limit rotation of the leg structure around the frontal pivot axis, a sagittal stop configured to limit rotation of the leg structure around the sagittal pivot axis, a transverse stop configured to limit rotation of the leg structure around the transverse pivot axis; and/or the orthosis is an exoskeleton.

The disclosure applies for example to exoskeletons, but also to any type of or orthosis comprising a hip structure and a leg structure.

DESCRIPTION OF THE FIGURES

Other features, objects and advantages will be revealed by the description that follows, which is purely illustrative and not limiting, and which must be read with reference to the appended drawings in which.

In all the figures, similar elements carry identical references.

DETAILED DESCRIPTION

Figure 1:
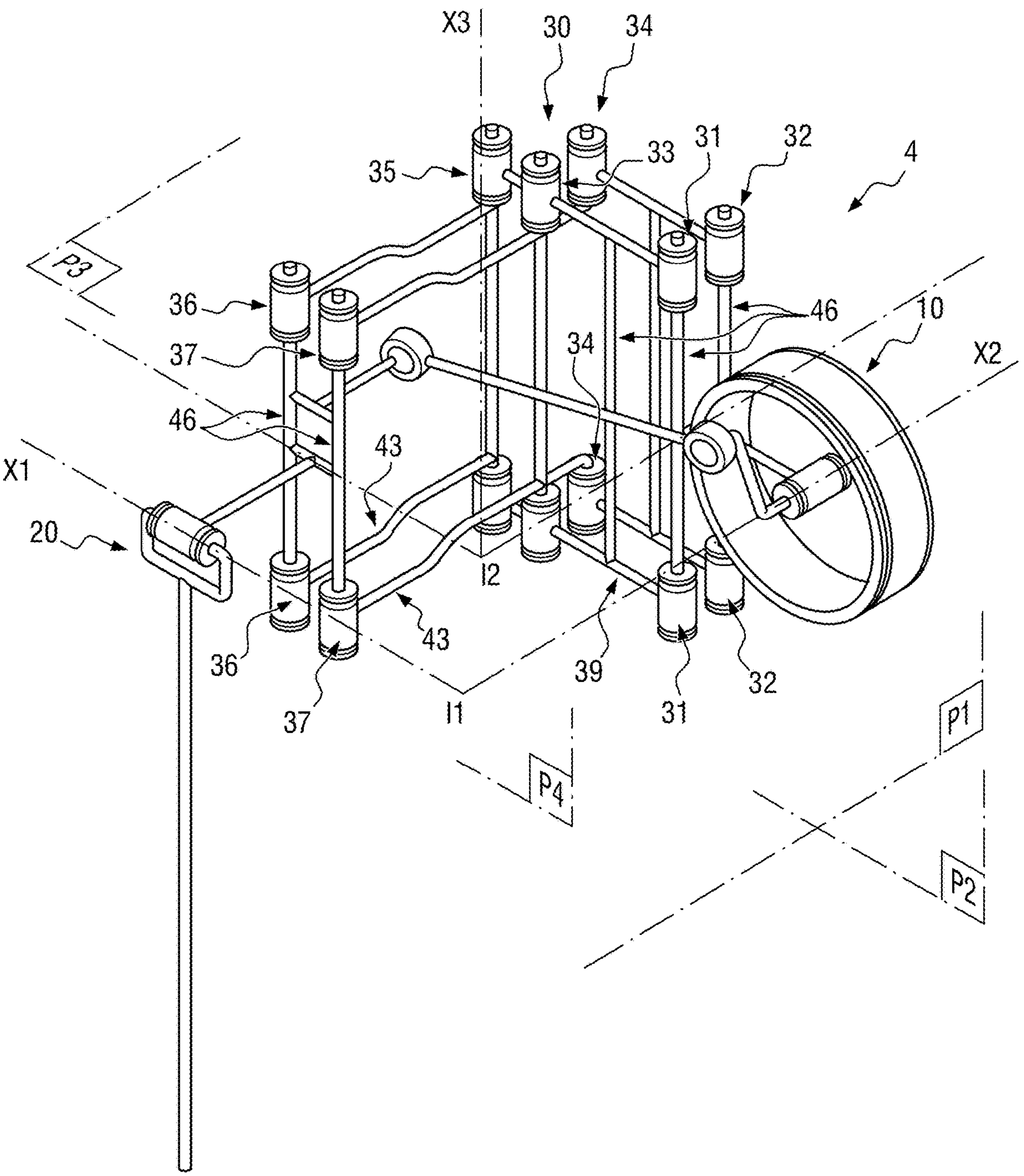
FIG. 1 is a kinematic model of an exemplary embodiment of a mechanical hip link for an orthosis conforming to an embodiment, when the orthosis is at rest.

An orthosis 1 comprises a hip structure 2 configured to position itself facing a hip of a user and a leg structure 3 configured to receive a leg of the user. The hip structure 2 and the leg structure 3 are configured to be connected by a mechanical hip link 4.

The leg structure 3 comprises an upper leg structure 3 configured to receive a thigh of a user, and optionally a lower leg structure 3 configured to receive a calf of the user. If applicable, the lower leg structure 3 and the upper leg structure 3 are connected by a mechanical knee link allowing movement of the lower leg structure 3 relative to the upper leg structure 3. The hip structure 2, for its part, extends laterally relative to the corresponding hip of the user.

In the following, the disclosure will be described in the case of an orthosis 1 comprising the hip structure 2 and a leg structure 3. The disclosure applies, however, to any orthosis 1 for the human or animal body comprising a hip structure 2 and a leg structure 3, for example an orthosis 1 comprising a right leg structure 3 and a left leg structure 3, with or without a lower leg structure 3, and if applicable with a foot structure 5 connected by a mechanical ankle link [to] each lower leg structure 3. The disclosure then applies symmetrically to the mechanical link connecting the hip structure 2 to the right leg structure 3 and to the left leg structure 3. Optionally, the orthosis 1 can also comprise a pelvis structure 6, configured to be positioned behind the kidneys of the user when he is wearing the orthosis 1 and which can be attached to the pelvis of the user by means of a harness or straps.

Figure 2:
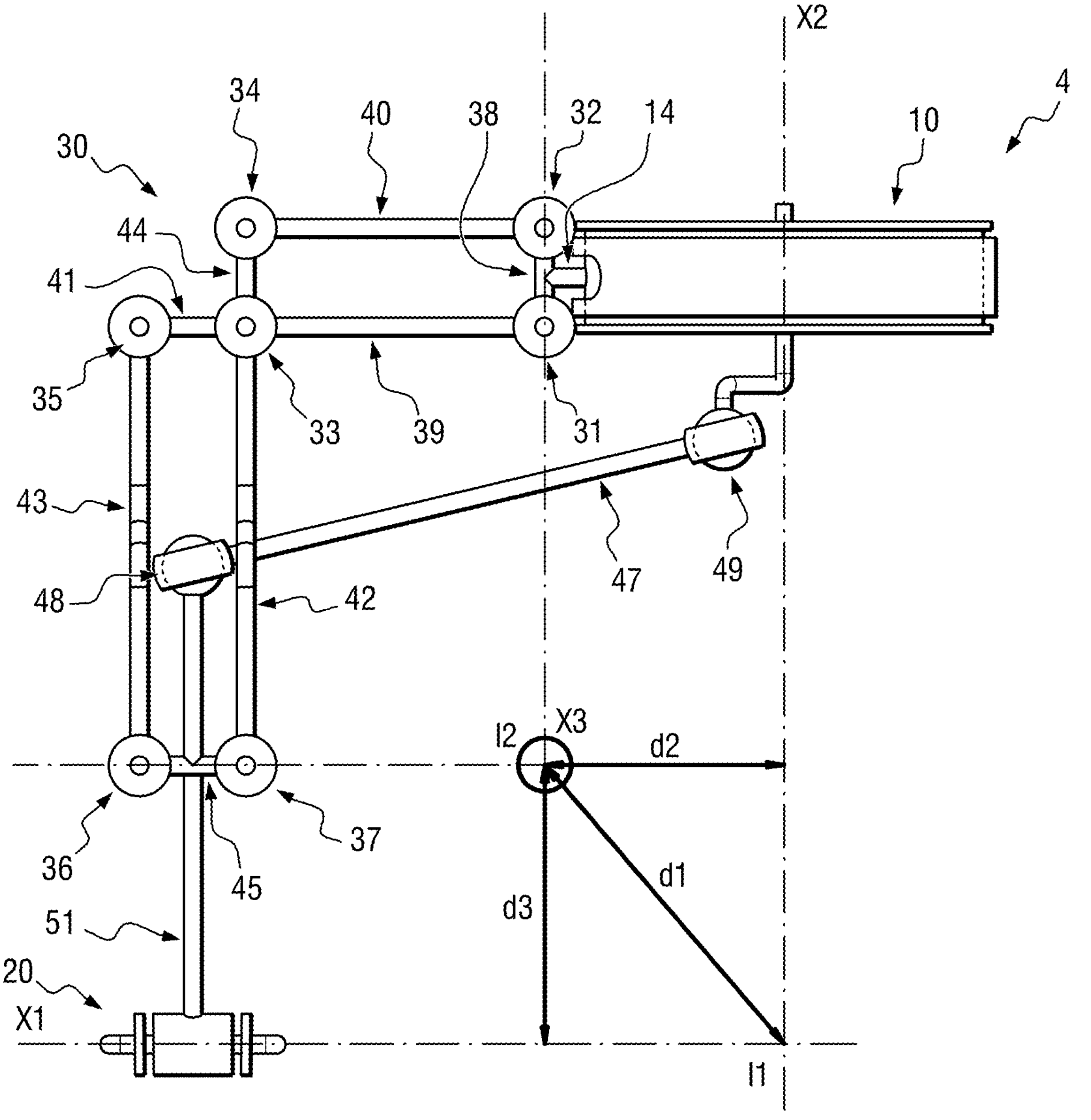
FIG. 2 is a top view of the kinematic model of FIG. 1.
Figure 3:
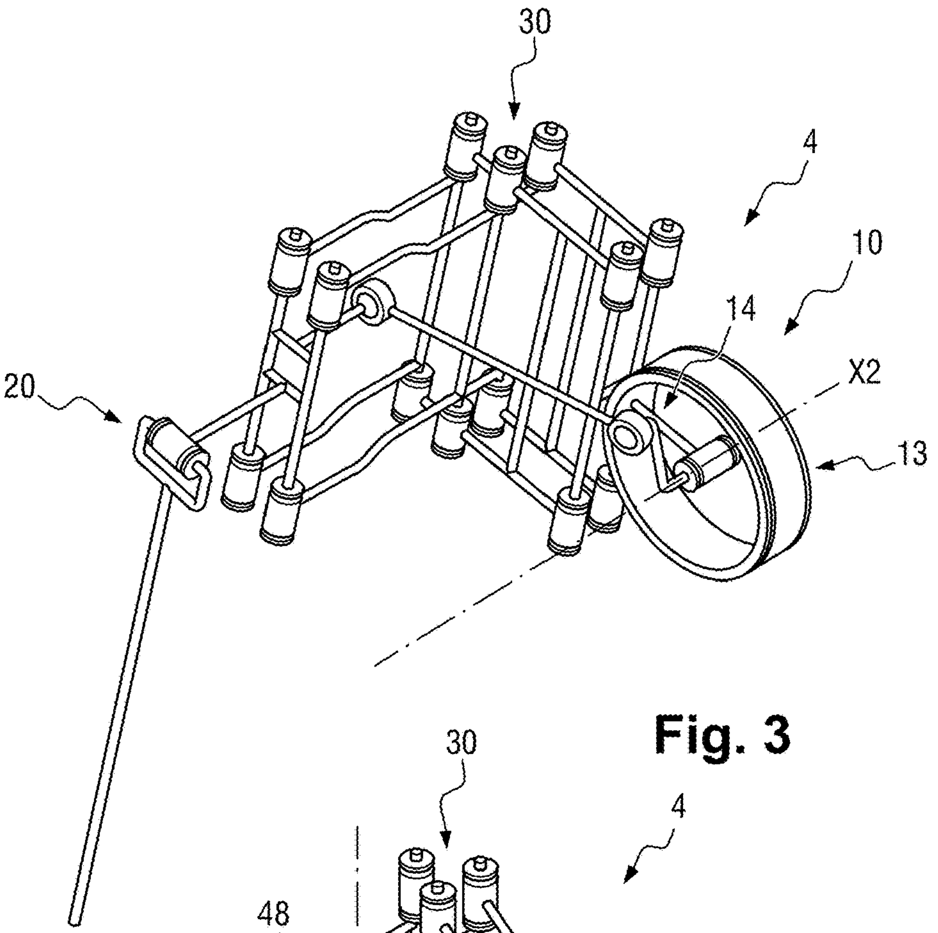
FIG. 3 corresponds to the kinematic model of FIG. 1 during a pure rotation movement around the frontal pivot axis of the orthosis.

The orthosis 1 will be described in the following in relation with reference planes and axes, and more particularly a sagittal plane P1, a transverse plane P3 and a frontal plane P2 of the orthosis 1. The extension direction of these plane is defined when the orthosis is worn by a user who is standing upright, feet together and parallel to one another. In the following, this position will be defined as the resting position of the orthosis 1 (or neutral position—see FIGS. 1 and 2).

When the orthosis 1 comprises two leg structures, the sagittal plane P1 corresponds to the vertical plane of symmetry of the orthosis 1, which passes through the center of the hip structure 2. The right leg structure 3 is then substantially symmetrical with the left leg structure 3 relative to the sagittal plane P1. It will be noted that the sagittal plane P1 of an orthosis 1, in conformity with the disclosure and comprising only a single leg structure 3, is positioned at the same location of the orthosis 1 as if the orthosis 1 comprised two leg structures. It is therefore in this sagittal plane P1 that the bending and extension movements of the leg structure 3 take place relative to the hip structure 2, linked for example to walking.

The frontal plane P2 of the orthosis 1 is normal to the sagittal plane P1 and divides the orthosis into two parts, an anterior (ventral) part and a posterior (dorsal) part. It is in this plane that the movements of abduction and adduction of the leg structure 3 take place relative to the hip structure 2, linked for example to hip swaying movements.

The transverse plane P3 of the orthosis 1 is normal to the sagittal plane P1 and to the frontal plane P2. It is parallel to the ground and divides the orthosis 1 into two parts, an upper part (toward the user's pelvis) and a lower part (toward the user's feet). It is in this plane that the internal and external rotation movements of the leg structure 3 take place relative to the hip structure 2, linked for example to torsion movements of the leg structure 3.

The mechanical hip link 4 comprises:

- a frontal pivot link 10 configured to allow rotation movement of the leg structure 3 relative to the hip structure 2 around a frontal pivot axis X2 which is normal to the frontal plane P2 of the orthosis 1;
- a sagittal pivot link 20 configured to allow rotation movement of the leg structure 3 relative to the hip structure 2 around a sagittal pivot axis X1 which is normal to the sagittal plane P1 of the orthosis 1 when the orthosis 1 is at rest; and
- a transverse pivot link 30 configured to allow rotation movement of the leg structure 3 relative to the hip structure 2 around a transverse pivot axis X3 which is normal to the transverse plane P3 of the orthosis 1 when the orthosis 1 is at rest.

The sagittal pivot axis X1 and the frontal pivot axis X2 are concurrent, i.e. they intersect at a first intersection point 11. Preferably, when a user wears the orthosis 1, at rest, this first intersection point 11 is conflated with the center of rotation of the articulation of the corresponding hip of the user (coxofemoral articulation which is similar to a spherical ball joint link).

The transverse pivot link 30 is composed of a plurality of pivot links 31-37 connected two by two by connecting rods 38-45 so as to form a virtual pivot link 30 so that the transverse pivot axis X3 intersects the volume delimited by the sagittal plane P1, by a plane P4 normal to the frontal pivot axis X2 and comprising the sagittal pivot axis X1, by the hip structure 2 and by the leg structure 3. In other words, the intersection 12 between the (transverse) pivot axis of the virtual pivot link 30 and the plane comprising the frontal X2 and sagittal X1 pivot axes is located in the volume which extends between the hip structure 2 and the leg structure 3, on the one hand, and between the sagittal X1 and frontal X2 pivot axes, on the other hand.

Here a "connecting rod" is understood to be a rigid part that is not deformable under normal conditions of use of the orthosis 1. The pivot links 31-37 connected by a given connecting rod 38-45 are therefore connected together fixedly so that the distance between their respective axes of rotation is constant under normal conditions of use.

The mechanical hip link 4 thus obtained is more ergonomical, in that the sagittal X1 and frontal X2 pivot axes correspond to the natural pivot axes of the articulation of the hip of the user and can be concurrent with these natural pivot axes. Moreover, the pivot axis X3 of the virtual pivot link 30 being near the center of rotation of the coxofemoral articulation of the hip, the parasitic movements likely to advance the pelvis of the user during a walking movement or spreading his leg outward are strongly limited. The articulation in external rotation can also be more ample, which confers three real degrees of freedom on the mechanical hip link 4 of the orthosis 1, allowing the user a stable walk (without necessitating crutches).

The production of the virtual pivot link 30 due to pivot links 31-37 connected in series by connecting rods 38-45 allows approaching the pivot axis X3 of the transverse pivot link 30 to the center of rotation of the coxofemoral articulation of the hip, without risking injuring the user and while dispensing with the need to place the pivot link in the body of the user. In fact, the decomposition of the transverse pivot link 30 into a plurality of pivot links 31-37 in series allows offsetting a portion of the articulation outside the volume occupied by the user while positioning the pivot axis resulting from this decomposition in this volume, i.e. substantially in proximity to the first intersection point 11, between the frontal pivot axis X2 and the sagittal pivot axis X1.

The transverse pivot axis X3 intersects the plane comprising the frontal pivot axis X2 and the sagittal pivot axis X1 at a second intersection point 12. The virtual pivot link 30 is then configured so that the distance d1 between this second intersection point 12 and the first intersection point 11 (between the sagittal X1 and frontal X2 pivot axes) is less than 150 mm when the orthosis 1 is at rest, preferably less than 120 mm, more preferably less than 100 mm, for example less than or equal to 92 mm, typically on the order of 70 mm. Moreover, the second intersection point 12 is located at a distance d2 less than or equal to 90 mm from the sagittal plane P1 of the orthosis 1 when the orthosis 1 is at rest, preferably less than or equal to 60 mm, more preferably less than or equal to 40 mm, for example at least equal to 0 mm and at most equal to 10 mm. The second intersection point 12 can then be located at a distance d3 less than or equal to 90 mm from the plane P4 (which is normal to the frontal pivot axis X2 and comprises the sagittal pivot axis X1 of the orthosis 1) when the orthosis 1 is at rest, preferably less than or equal to 70 mm. It will be noted that the transverse pivot axis X3 is preferably normal to the plane comprising the sagittal pivot axis X1 and the frontal pivot axis X2.

In this configuration, the possible angle of articulation of the virtual pivot link 30, without parasitic movements being noticeable by the user, is at least equal to 40° when the distance d1 is on the order of 70 mm, the distance d2 is comprised between 0 mm and 10 mm and the distance d3 is less than or equal to 70 mm.

The orthosis 1 also comprises actuators 12, 22, 32 configured to independently actuate the frontal pivot link 10, the transverse pivot link 30 and the sagittal pivot link 20. The independent actuation of the different pivot links 10, 20, 30 in fact allows simplifying the control of the mechanical hip link 4. To this end, the orthosis 1 comprises a transverse actuator 32 configured to actuate the transverse pivot link 30, a frontal actuator 12 configured to actuate the frontal pivot link 10 and a sagittal actuator 22 configured to actuate the sagittal pivot link 20, these three actuators 12, 22, 32 being independent from one another. Each actuator 12, 22, 32 comprises, in a manner known per se, a motor configured to rotate an output shaft 15, 24, to which is connected (directly or indirectly) the corresponding pivot link 10, 20, 30.

Moreover, the frontal pivot link 10 is mechanically connected to the hip structure 2, the sagittal pivot link 20 is mechanically connected to the leg structure 3 and the transverse pivot link 30 is mechanically connected to the frontal pivot link 10, and to the sagittal pivot link 20. The frontal 10, transverse 30 and sagittal 20 pivot links are therefore mounted in series. In addition, the sagittal actuator 22 is mounted on the transverse pivot link 30 and the transverse actuator 32 is mounted on the frontal pivot link 10. This configuration thus allows the use of independent mechanical stops 19*a-b*, 25*a-b*, 52 for each pivot axis X1, X2, X3 of the mechanical hip link 4, which guarantees the safety of the patient in all situations because these mechanical stops 19*a-b*, 25*a-b*, 52 prevent the orthosis 1 from carrying out movements extending beyond the articulations of the user's articulations, even during a loss of control of the actuators 12, 22, 32.

The transverse pivot link 30 can comprise in particular:

- two first pivot links 31, 32 connected together by a first connecting rod 38;
- a second and a third pivot link 33, 34 each connected to a corresponding first pivot link 31, 32 by a second and a third connecting rod 39, 40, respectively, the second and the third connecting rods 39, 40 having the same length;
- a fourth pivot link 35 connected to the second pivot link 33 by a fourth connecting rod 41 which is fixedly joined to the second connecting rod 39;
- a fifth and a sixth pivot link 36, 37 connected respectively to the second pivot link 33 and to the fourth pivot link 35 by a fifth and a sixth connecting rod 42, 43, respectively, the fifth and the sixth connecting rods 42, 43 having the same length;
- a seventh connecting rod 44 connecting the second and the third pivot link 33, 34 and being fixedly joined to the connecting rod 42; and
- an eighth connecting rod 45 connecting the fifth and the sixth pivot link 36, 37.

The length of the eighth connecting rod 45 is substantially equal to the length of the fourth connecting rod 41 so that the gap between the pivot axes of the fifth and sixth pivot links 36, 37 is substantially equal to the gap between the pivot axes of the second and third pivot links 33, 34. Likewise, the length of the first connecting rod 38 is substantially equal to the length of the seventh connecting rod 44 so that the gap between the pivot axes of the first pivot links 31, 32 is substantially equal to the gap between the pivot axes of the second and third pivot links 33, 34.

When the orthosis 1 is at rest, the pivot axes of the second, third and fifth pivot links 33, 34, 37 are aligned. Likewise, the pivot axes of the first pivot link 31 which is connected to the second connecting rod 39, and of the second and fourth pivot links 33, 35, are aligned.

In one embodiment, each pivot link 31-37 and at least one portion of the connecting rods 39-43 are doubled in order to increase the rigidity of the transverse pivot link 30, in particular with respect to the actions of the ground. To this end, each pivot link 31-37 comprises an upper pivot link and a lower pivot link (see FIGS. 1 and 3 to 5), the pivot axes of which are conflated and which are connected two by two by a plurality of vertical connecting rods 46. The upper pivot links 31-37 are also connected two by two by upper connecting rods 38-45 and the lower pivot links 31-37 are connected two by two by lower connecting rods 39-43. It will be noted that the number of upper 38-45 and lower 39-43 connecting rods can be different.

The transverse pivot link 30 being mounted on the frontal pivot link 10, the torque and the movement speed of the transverse pivot link 30 depend on the position of said link 30.

Figure 6:
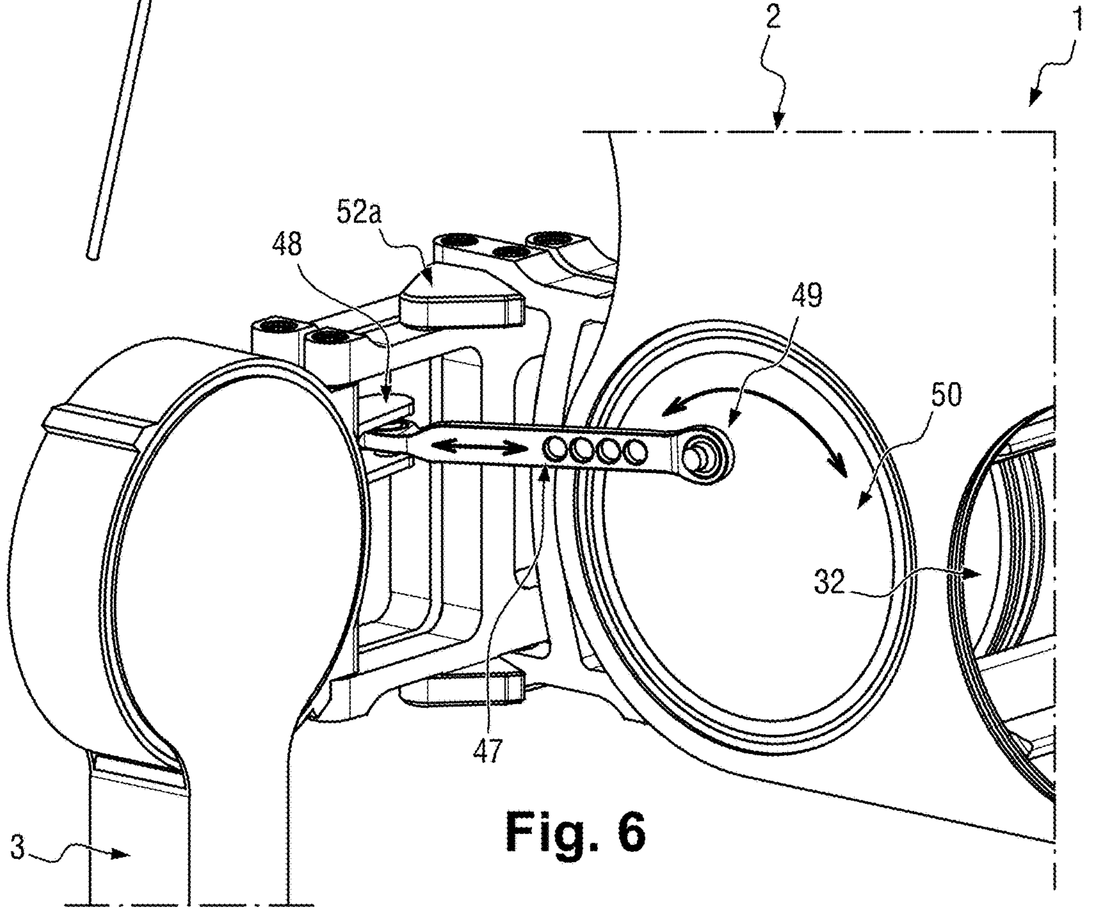
FIG. 6 is a simplified perspective view of one embodiment of an orthosis conforming to an embodiment, illustrating the actuation of the transverse mechanical link of the orthosis.
Figure 7:
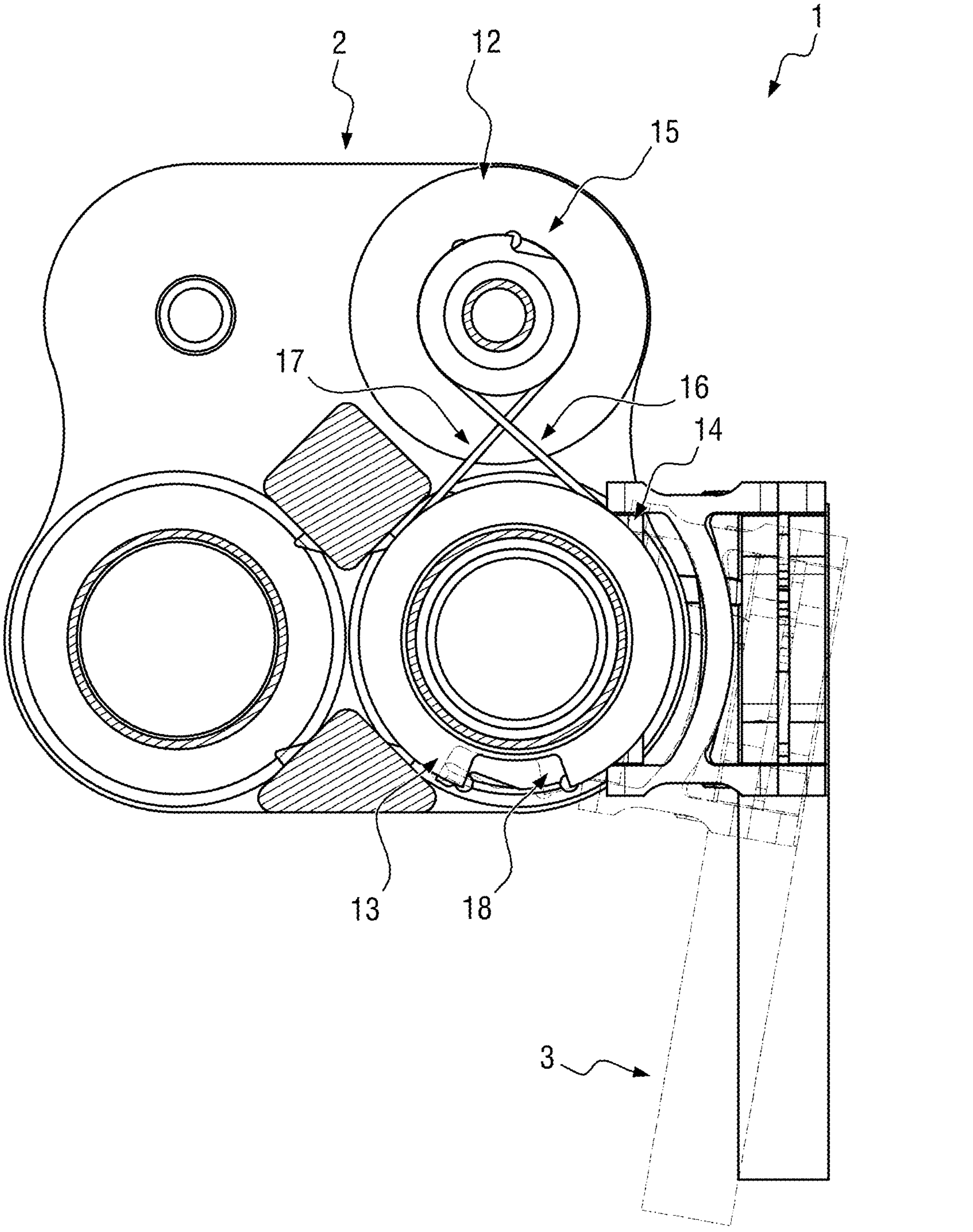
FIG. 7 is a simplified dorsal view of an exemplary embodiment of an orthosis conforming to an embodiment, illustrating an example of actuation of the frontal mechanical link of the orthosis, the leg structure being illustrated in two different positions.
Figure 8:
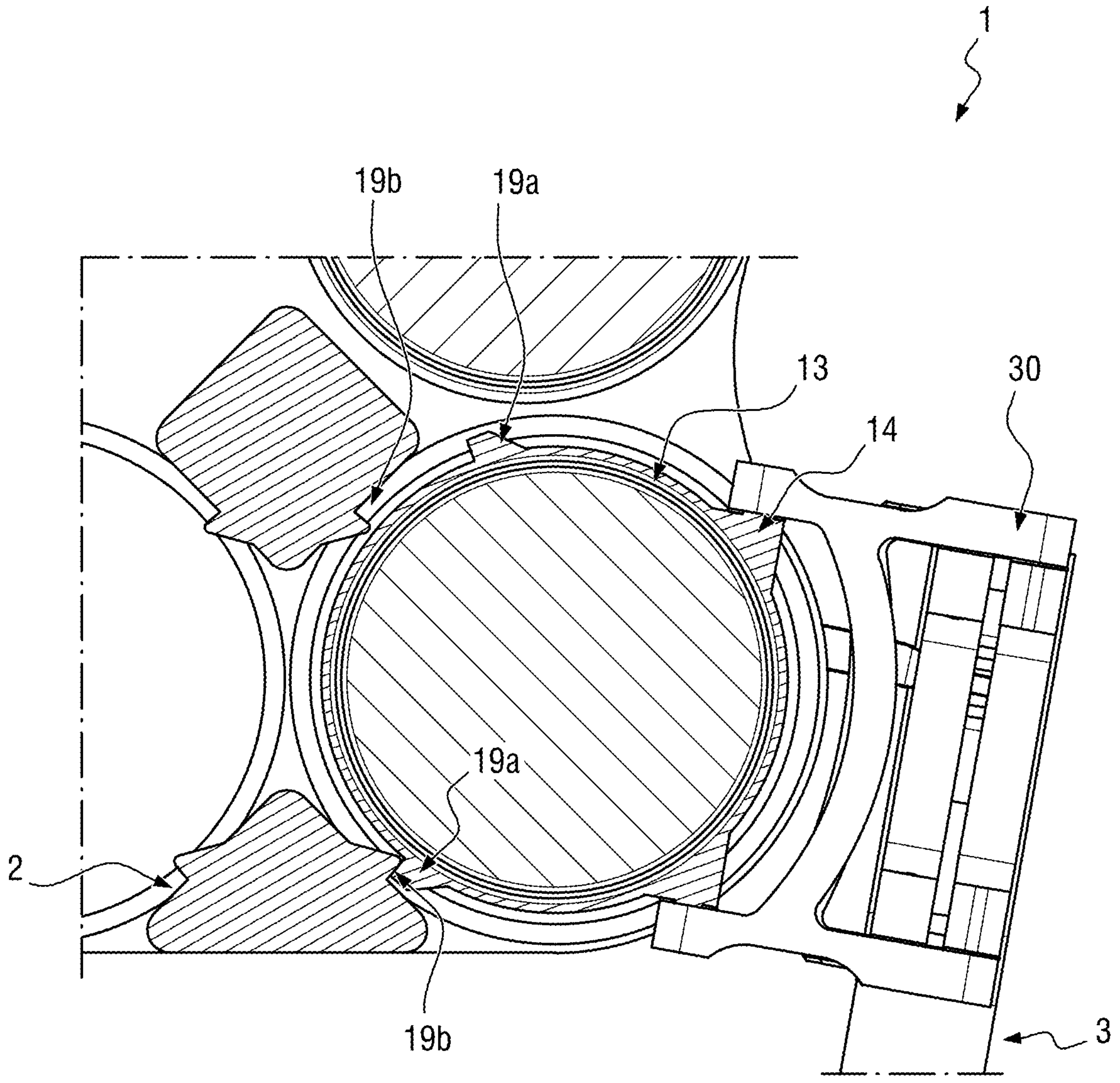
FIG. 8 is a simplified dorsal view of an exemplary embodiment of an orthosis conforming to an embodiment, illustrating an example of mechanical stops in the frontal pivot link.

The frontal pivot link 10 can for example comprise a pulley 13 mounted in the hip structure 2 and centered on the frontal pivot axis X2, which is connected fixedly to the leg structure 3 by a frontal actuating connecting rod 14 (hereafter frontal connecting rod 14—see FIGS. 2 and 6 in particular) so that the rotation of the pulley 13 relative to the hip structure 2 drives the rotation of the leg structure 3 around the frontal pivot axis X2. The pulley 13 can be mounted on the output shaft 15 (or if applicable a one-piece pulley with the output shaft 15) of the frontal actuator 12. As a variant, the output shaft 15 of the frontal actuator 12 can be offset in the hip structure 2 relative to the frontal pivot axis X2 and drive the pulley 13 by means of cables 16, 17. One example of offset driving has for example been illustrated in FIG. 7. The output shaft 15 of the frontal actuator 12 is offset relative to the frontal pivot axis X2 and extends above the pulley 13. A first cable 16 connects the output shaft 15 to the pulley 13 so as to pivot the pulley in a first direction around the frontal pivot axis X2, and a second cable 17 connects the pulley 13 to the output shaft 15 so as to pivot the pulley 13 in a second direction around the pivot axis X2. The cables 16, 17 intersect at an intermediate position between the output shaft 15 and the pulley 13 so that the first direction and the second direction are opposite.

The offset actuation of the frontal pivot link 10 allows reducing the bulk of the actuation of the mechanical hip link 4. The use of cables 16, 17 also allows increasing the reduction ratio of the frontal actuator motor 12 while reducing its size, which is all the more relevant in the context of the frontal pivot link 10, in that the necessary torque to be applied to this link 10 is greater than that required for the transverse 30 and sagittal 20 pivot links. The reduction ratio is defined by the diameter of the pulley 13 and of the portion of the output shaft 15 to which the cables 16, 17 are attached. The output shaft 15 (or if applicable the single-piece pulley with the output shaft 15 and to which the cables 16, 17 are attached) can for example have a diameter twice as small as the diameter of the pulley 13. Optionally, the orthosis 1 comprises a system 18 for pre-loading the tension of the cables 16, 17 integrated into the hip structure 2, configured to apply tension on the cables 16, 17 and thus guarantee the accuracy of the actuation of the frontal pivot link 10. The pre-loading system 18 can in particular comprise a screw system in order to adjust the tension applied to each cable 16, 17.

The transverse pivot link 30 is connected to the frontal connecting rod 14 of the frontal pivot link 10. The pure rotation of the leg structure 3 around the frontal pivot axis X2 thus has the effect of pivoting the transverse pivot link 30 and the sagittal pivot link 20 around the frontal pivot axis X2.

The transverse actuator 32 can comprise a first transverse actuating connecting rod 47 (hereafter, first transverse connecting rod 47) including a first end connected to the transverse pivot link 30 by means of a first ball joint link 48 and a second end connected to the hip structure 2 by means of a second ball joint link 49.

In one embodiment, the hip structure 2 comprises an actuating turntable 50 mounted coaxially with the frontal pivot axis X2 in the hip structure 2 so as to be movable in rotation around the frontal pivot axis X2. The turntable 50 is axially symmetrical and is connected to the output shaft of the transverse actuator 32. The turntable 500 can, if applicable, be mounted within the pulley 13 of the frontal pivot link 10. The second ball joint link 49 is then attached to the turntable 50 while being offset relative to the frontal pivot axis X2 in order to create a connecting rod-crank effect (see FIGS. 2 and 6 for example). In this manner, the rotation of the turntable 50 relative the hip structure 2 has the effect of moving the first transverse connecting rod 47 relative to the hip structure 2. The first ball joint link 48, for its part, is mounted on a second transverse actuating connecting rod 51 (hereafter second transverse connecting rod 51) of the transverse pivot link 30, which can for example be mounted on the eighth connecting rod 45. Finally, in the exemplary embodiment illustrated in the figures, the first transverse connecting rod 47 is mounted on the output of the frontal connecting rod 14 of the frontal pivot link 10. In other words, the transverse pivot link 30 is mounted on the output of the frontal pivot link 10.

Figure 4:
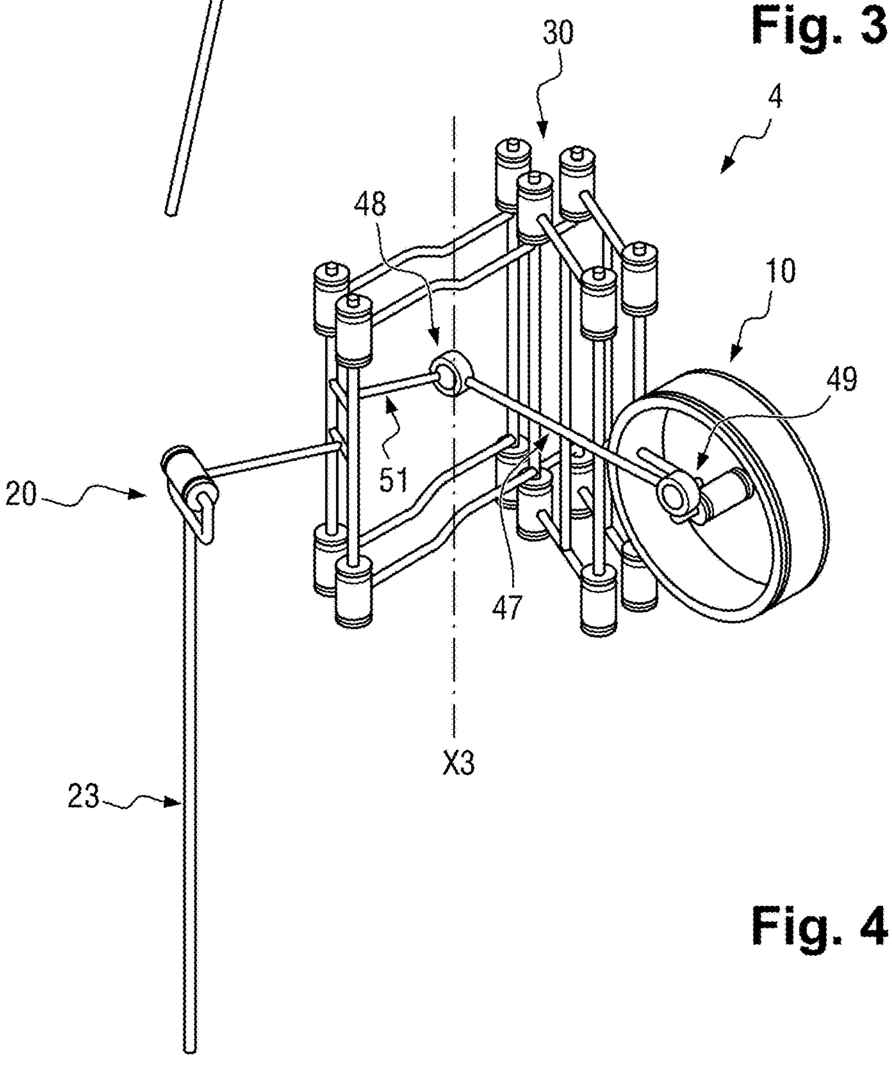
FIG. 4 corresponds to the kinematic model of FIG. 1 during a pure rotation movement around the transverse pivot axis of the orthosis.
Figure 5:
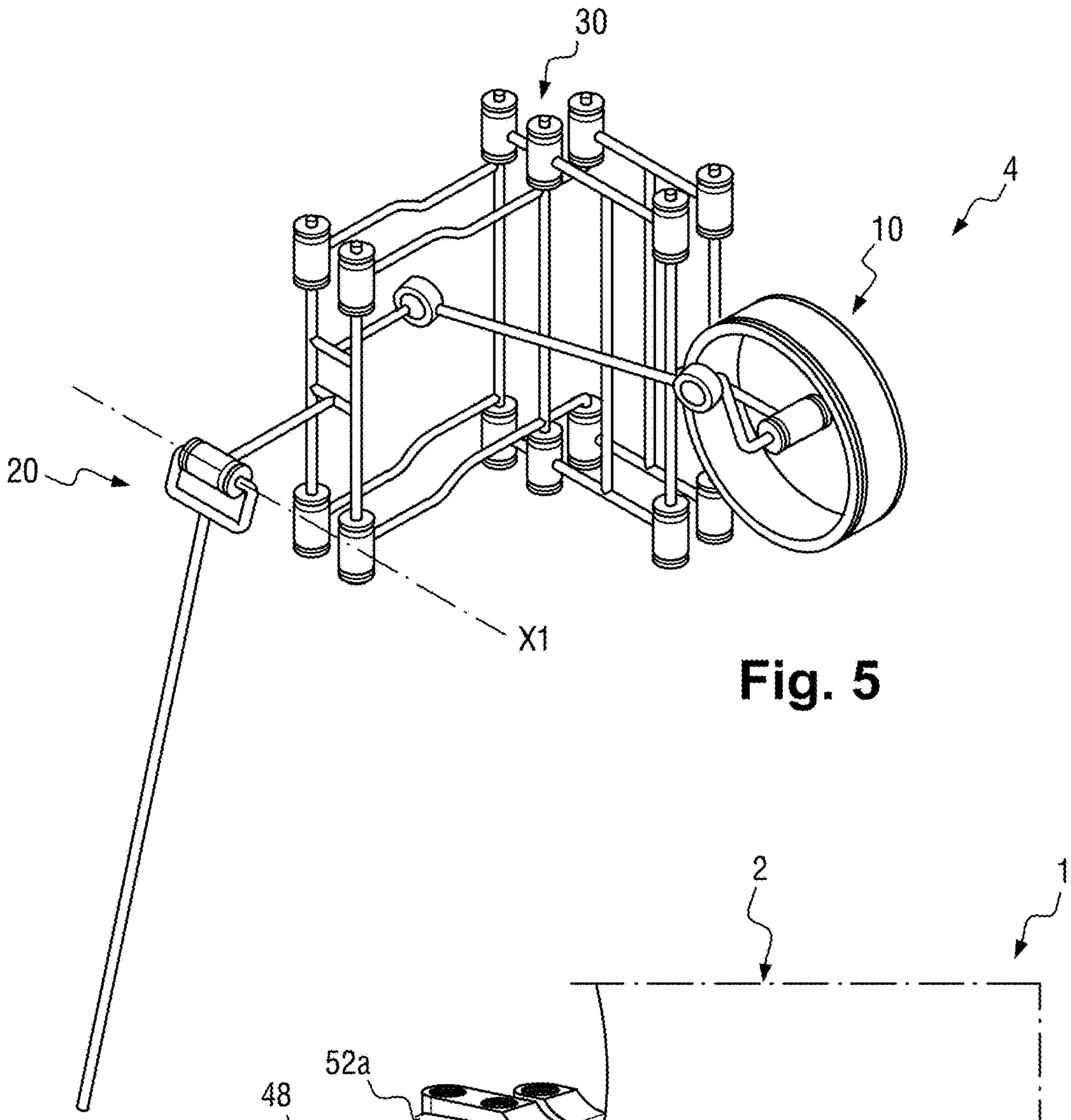
FIG. 5 corresponds to the kinematic model of FIG. 1 during a pure rotation movement around the sagittal pivot axis of the orthosis.

When the frontal pivot link 10 (and therefore the frontal connecting rod 14) is fixed, the movement of the turntable 50 relative to the hip structure 2 (and, if applicable, to the pulley 13 of the frontal pivot link 10) by the motor of the transverse actuator 32 has the effect of pushing or pulling (depending on the direction of rotation of the turntable 50) on the first transverse connecting rod 47 due to the connecting rod-crank system and therefore moving the second transverse connecting rod 51 (see FIG. 4). The transverse pivot link 30 then turns around its pivot axis X3. In addition, the sagittal pivot link 20 being mounted on the output of the transverse pivot link 30, the pure rotation of the leg structure 3 around the transverse pivot axis X3 has the effect of pivoting the sagittal pivot link 20 around the transverse pivot axis X3.

The sagittal pivot link 20 comprises a sagittal connecting rod 23 mounted fixedly on one of the connecting rods 38-45, 47, 51 of the transverse pivot link 30, typically the second transverse connecting rod 51 and/or the eighth connecting rod 45. The sagittal connecting rod 23 can, if applicable, be monolithic with the second transverse connecting rod 51 and/or the eighth connecting rod 45. The pivot axis X1 of the sagittal pivot link 20 moves therefore with a center of rotation of the first ball joint link 48.

The output shaft 24 of the sagittal actuator 22 can be coaxial with the sagittal pivot axis X1 and be configured to rotate (directly or indirectly, via an associated turntable) the leg structure 3 around the sagittal pivot axis X1. The rotation of the output shaft 24 then has the effect of turning the leg structure 3 relative to the sagittal connecting rod 23 around the sagittal pivot axis X1.

As previously indicated, the orthosis 1 can also comprise mechanical stops 19*a*-*b*, 25*a*-*b*, 52 configured to limit the articulation of the mechanical hip link 4 and protect the user, even in case of breakdown of one of the actuators 12, 22, 32. These mechanical stops 19*a*-*b*, 25*a*-b, 25*b*, 52 are independent. Moreover they are designed so as to be easily interchangeable to allow customization of the articular articulations depending on the articulation capacities of each user.

The orthosis 1 can comprise at least one of the following mechanical stops 19*a*-*b*, 25*a*-*b*, 25*b*, 52: a frontal stop 19*a*-*b* configured to limit rotation of the leg structure 3 around the frontal pivot axis X2, a sagittal stop 25*a*-*b* configured to limit rotation of the leg structure 3 around the sagittal pivot axis X1, a transverse stop 52 configured to limit rotation of the leg structure 3 around the transverse pivot axis X3.

The mechanical stop 19*a*-*b* of the frontal pivot link 10 can in particular comprise at least one lug 19*a* attached to the pulley 13 so as to protrude radially relative to the pulley 13, and as many protuberances 19*b* attached to the hip structure 2, each lug 19*a* being configured to come into contact with a corresponding protuberance 19*b* when the leg structure 3 attains the maximum allowable articulation around the front pivot axis X2. Preferably, the orthosis 1 comprises a high mechanical stop 19*a*-*b* configured to prevent rotation in a first direction of the frontal pivot link 10 beyond a first maximum articulation, for example +20° relative to the neutral position, at rest (abduction movement of the leg structure 3), and a low mechanical stop 19*a*-*b* configured to prevent rotation in a second direction of the frontal pivot link 10, opposite to the first direction of rotation, beyond a second maximum articulation, for example −10° relative to the neutral position, at rest (adduction movement of the leg structure 3).

The mechanical stop 52 of the transverse pivot link 30 can comprise a lug 52*a* attached to one of the connecting rods 38-45 forming the transverse pivot link 30, for example the fifth connecting rod 42, and configured to come into abutment against a protuberance fixed to or forming at least one other of the connecting rods 38-45 of the transverse pivot link 30, for example the second connecting rod 39 (which is integral with the fourth connecting rod 41). Preferably the orthosis 1 comprises an internal mechanical stop configured to prevent rotation in a first direction of the transverse pivot link 30 beyond a first maximum articulation (the corresponding protuberance then being attached to or formed by the second connecting rod 39), for example −10° relative to the neutral position, at rest (internal rotation movement of the leg structure 3), and an external mechanical stop configured to prevent rotation in a second direction of the transverse pivot link 30, opposite to the first direction of rotation, beyond a second maximum articulation (the corresponding protuberance then being attached to or formed by the sixth connecting rod 43), for example +30° relative to the neutral position, at rest (external rotation movement of the leg structure 3).

Figure 9:
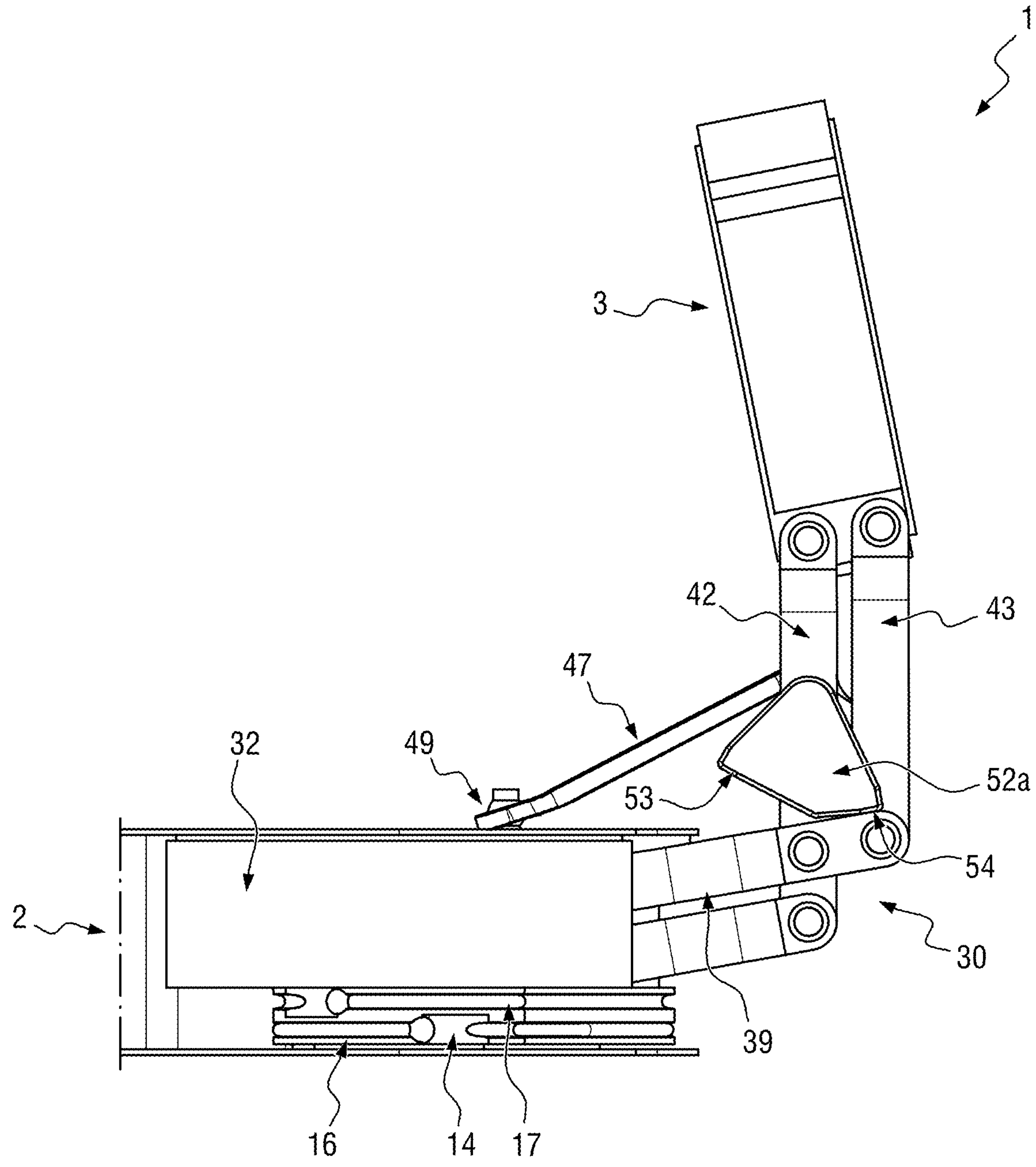
FIG. 9 is a simplified top view of an exemplary embodiment of an orthosis conforming to an embodiment, illustrating an example of a mechanical stop in the transverse pivot link.

For example, the lug 52*a* can comprise a plaque applied and attached to the fifth connecting rod 42 and having a first face 53 forming an internal mechanical stop and configured to come into contact with the second, facing connecting rod 39, and a second face 54 opposite to the first face 53, forming an external mechanical stop configured to come into contact with the fourth connecting rod 41 (see FIG. 9 for example).

Preferably, when the pivot links 31-37 of the transverse pivot link 30 are doubled, each mechanical stop 52 can also be symmetrically doubled (high/low) in order to increase the durability of the stop system. The orthosis 1 then comprises upper mechanical stops, attached to the upper connecting rods 38-45 and lower mechanical stops, attached to the corresponding lower connecting rods 39-43, in line with the upper mechanical stops.

The mechanical stop 25*a*-*b* of the sagittal pivot link 20 can, in a similar manner to the mechanical stop of the frontal pivot link 10, comprise at least one lug 24*a* that moves with the output shaft 24 of the sagittal actuator 22, so as to protrude radially relative to the output shaft 24, and as many protuberances 25*b* mounted fixedly relative to the sagittal connecting rod 23, each lug 25*a* being configured to come into contact with a corresponding protuberance 25*b* when the leg structure 3 attains the maximum allowable articulation around the sagittal pivot axis X1. Preferably, the orthosis 1 comprises a high mechanical stop 25*a*-*b* configured to prevent rotation in a first direction of the sagittal pivot link 20 beyond a first maximum articulation, for example +115° relative to the neutral position, at rest (bending movement of the leg structure 3) and a low mechanical stop 25*a*-*b* configured to prevent rotation in a second direction of the sagittal pivot link, opposite to the first direction of rotation, beyond a second maximum articulation, for example −15° relative to the neutral position, at rest (extension movement of the leg structure 3).

Figure 10:
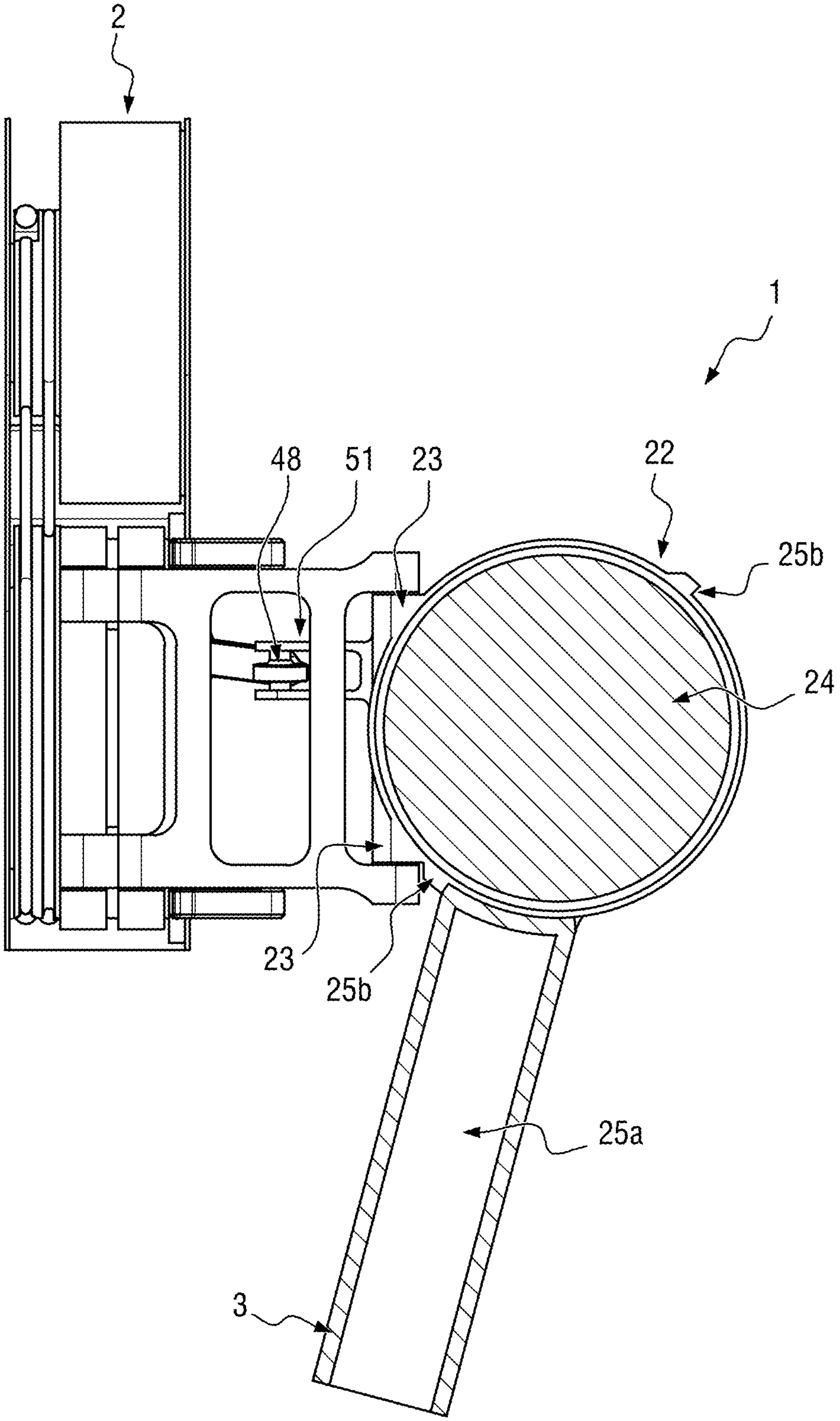
FIG. 10 is a simplified side view of an exemplary embodiment of an orthosis conforming to an embodiment, illustrating an example of mechanical stops in the sagittal pivot link.
Figure 11:
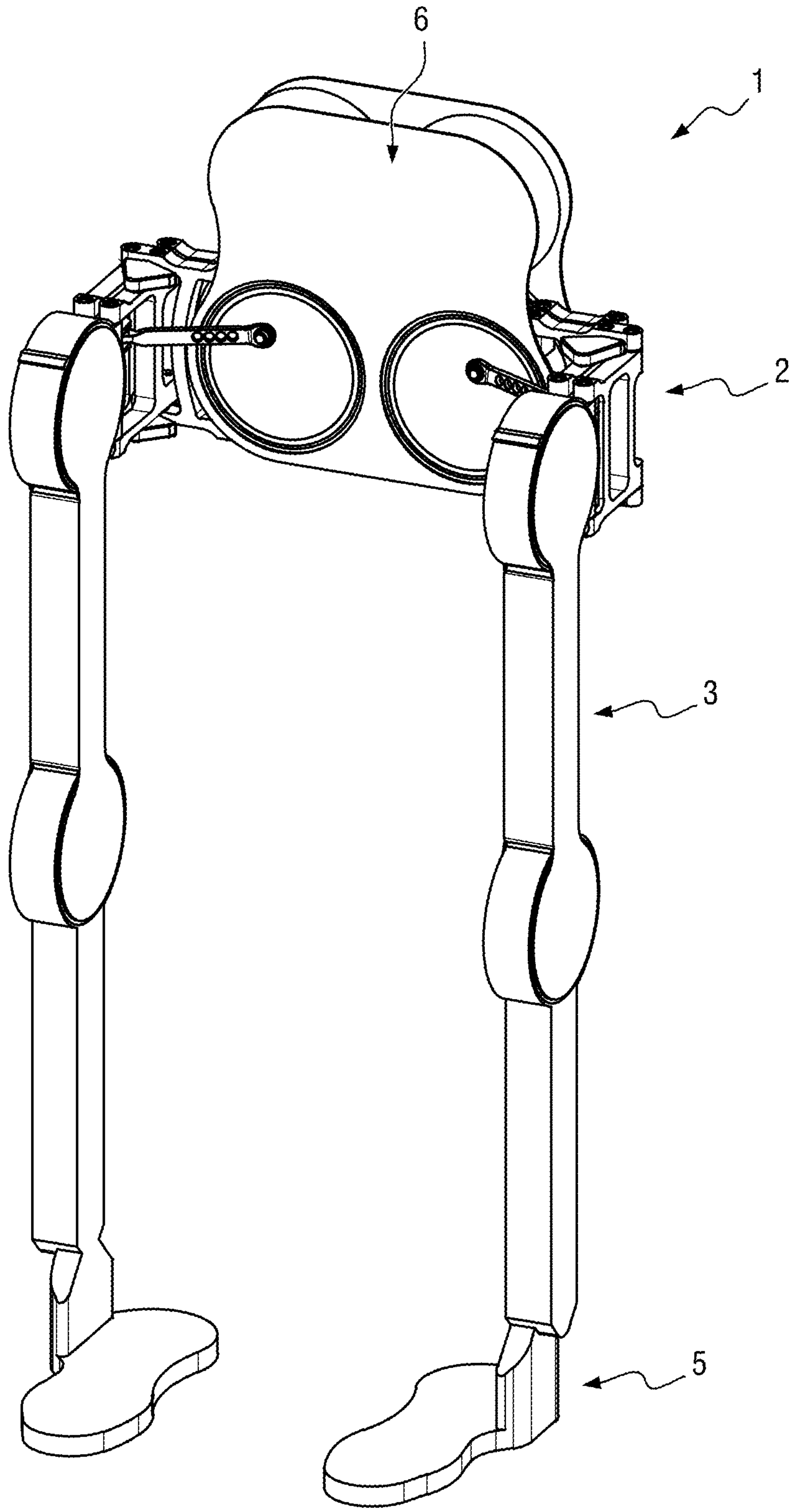
FIG. 11 is a simplified view of an example of an exoskeleton comprising a mechanical hip link conforming to an embodiment.

For example, the lugs 24*a* of the high and low mechanical stops can be formed by two opposite faces of a connecting rod of the leg structure (see FIG. 10).

The invention claimed is:

1. An orthosis comprising:

a mechanical hip link connecting a hip structure configured to be positioned facing a hip of a user; and a leg structure configured to receive a leg of the user, wherein the mechanical hip link comprises a frontal pivot link configured to allow rotation movement of the leg structure relative to the hip structure about a frontal pivot axis of the orthosis, a sagittal pivot link configured to allow rotation movement of the leg structure relative to the hip structure about a sagittal pivot axis of the orthosis and a transverse pivot link configured to allow rotation movement of the leg structure relative to the hip structure about a transverse pivot axis of the orthosis;

wherein the sagittal pivot axis and the frontal pivot axis are concurrent; and wherein the transverse pivot link is composed of a plurality of pivot links connected two by two by connecting rods so as to form a virtual pivot link so that the transverse pivot axis intersects a volume delimited by the sagittal plane, by a plane normal to the frontal pivot axis and comprises the sagittal pivot axis, by the hip structure and by the leg structure.

2. The orthosis according to claim 1, wherein the transverse pivot axis is normal to a plane formed by the frontal pivot axis and the sagittal pivot axis, a first intersection point defined by the intersection between the plane and the transverse pivot axis being located at a distance less than 150 mm from a second intersection point defined by the intersection of the sagittal and frontal pivot axes.

3. The orthosis according to claim 2, wherein the first intersection point is located at a distance less than or equal to 90 mm from the sagittal plane of the orthosis.

4. The orthosis according to claim 2, wherein the first intersection point is located at a distance less than or equal to 90 mm from a plane parallel to the frontal plane of the orthosis and comprising the sagittal pivot axis.

5. The orthosis according to claim 2, wherein first intersection point and the is located at a distance less than 120 mm from the second intersection point.

6. The orthosis according to claim 2, wherein first intersection point and the is located at a distance less than or equal to 92 mm from the second intersection point.

7. The orthosis according to claim 2, wherein the first intersection point is located at a distance less than or equal to 40 mm from the sagittal plane of the orthosis.

8. The orthosis according to claim 2, wherein the first intersection point is located at a distance greater than or equal to 0 mm and less than or equal to 10 mm.

9. The orthosis according to claim 1, wherein the pivot links composing the transverse pivot link comprise:

two first pivot links connected by a first connecting rod;

a second and a third pivot link each connected to a corresponding first pivot link by a second and a third connecting rod, respectively, the second and the third connecting rods having the same length;

a fourth pivot link connected to the second pivot link by a fourth connecting rod which is fixedly joined to the second connecting rod;

a fifth and a sixth pivot link connected respectively to the second pivot link and to the fourth pivot link by a fifth and a sixth connecting rod, respectively, the fifth and the sixth connecting rods having the same length;

a seventh connecting rod connecting the second and the third pivot link and being fixedly joined to the fifth connecting rod; and an eighth connecting rod connecting the fifth and the sixth pivot link.

10. The orthosis according to claim 1, wherein the frontal pivot link is mechanically connected to the hip structure, the sagittal pivot link is mechanically connected to the leg structure, and the transverse pivot link is mechanically connected to the frontal pivot link and to the sagittal pivot link.

11. The orthosis according to claim 1, also comprising a transverse actuator configured to actuate the transverse pivot link, a frontal actuator configured to actuate the frontal pivot link and a sagittal actuator configured to actuate the sagittal pivot link, the transverse actuator, the frontal actuator and the sagittal actuator being independent of one another.

12. The orthosis according to claim 1, also comprising a transverse actuator configured to actuate the transverse pivot link, the transverse actuator comprising an actuating connecting rod including a first end connected to the transverse pivot link by means of a first ball joint link and a second end connected to the hip structure by means of a second ball joint link.

13. The orthosis according to claim 12, wherein the second ball joint link is offset relative to the frontal pivot axis.

14. The orthosis according to claim 12, wherein the transverse actuator comprises an actuating turntable coaxial with the frontal pivot axis.

15. The orthosis according to claim 14, wherein the second ball joint link is connected to the actuating turntable and is offset relative to the frontal pivot axis.

16. The orthosis according to claim 12, wherein the sagittal pivot axis of the sagittal pivot link moves with a center of rotation of the first ball joint link.

17. The orthosis according to claim 1, also comprising a frontal actuator configured to actuate the frontal pivot link, the frontal actuator being offset relative to the frontal pivot axis.

18. The orthosis according to claim 17, wherein the frontal actuator comprises two cables mounted crossing on an output shaft of the frontal actuator and mounted on the frontal pivot link in order to pivot the frontal pivot link around the frontal pivot axis.

19. The orthosis according to claim 1, also comprising at least one of the following mechanical stops: a frontal stop configured to limit rotation of the leg structure around the frontal pivot axis, a sagittal stop configured to limit rotation of the leg structure around the sagittal pivot axis, a transverse stop configured to limit rotation of the leg structure around the transverse pivot axis.

20. The orthosis according to claim 1, said orthosis being an exoskeleton.

* * * * *